(12) United States Patent
Palomino

(10) Patent No.: US 11,234,924 B1
(45) Date of Patent: Feb. 1, 2022

(54) SKIN MOISTURIZING FORMULATION

(71) Applicant: Tova Palomino, Coral Springs, FL (US)

(72) Inventor: Tova Palomino, Coral Springs, FL (US)

( * ) Notice: Subject to any disclaimer, the term of this patent is extended or adjusted under 35 U.S.C. 154(b) by 0 days.

(21) Appl. No.: 16/922,234

(22) Filed: Jul. 7, 2020

(51) Int. Cl.
| | |
|---|---|
| *A61K 8/92* | (2006.01) |
| *A61Q 19/00* | (2006.01) |
| *A61Q 17/04* | (2006.01) |
| *A61Q 19/08* | (2006.01) |
| *A61Q 19/10* | (2006.01) |

(52) U.S. Cl.
CPC ............... *A61K 8/922* (2013.01); *A61Q 17/04* (2013.01); *A61Q 19/007* (2013.01); *A61Q 19/08* (2013.01); *A61Q 19/10* (2013.01)

(58) Field of Classification Search
CPC ................................. A61Q 19/00; A61K 36/00
See application file for complete search history.

(56) References Cited

U.S. PATENT DOCUMENTS

| | | | | |
|---|---|---|---|---|
| 2004/0258783 | A1* | 12/2004 | Millou | A61K 8/922 424/778 |
| 2008/0279902 | A1* | 11/2008 | Luria | A61K 33/00 424/401 |

OTHER PUBLICATIONS

HudaBeauty (OMG! We May Have Just Started a DIY Revolution!, Apr. 2018, by HB Team) (Year: 2018).*

* cited by examiner

*Primary Examiner* — Mark V Stevens
(74) *Attorney, Agent, or Firm* — Malloy and Malloy PL; Jennie S. Malloy

(57) ABSTRACT

The present invention discloses an organic skin moisturizer, which extends and improves the skin cells. The composition is dermatologically acceptable and is capable of moisturizing skin for at least twelve hours after topical application to skin even after multiple washings of the skin.

1 Claim, No Drawings

SKIN MOISTURIZING FORMULATION

BACKGROUND

Copyright Notice

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention pertains generally to a moisturizing skin cream. More particularly, the present invention is particularly, but not exclusively, useful for a moisturizing skin cream suitable for use on the face and neck.

DESCRIPTION OF THE RELATED ART

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or interred thereupon.

The skin is the largest organ of the human body, primarily functioning to protect the body's internal organs from the outside environment. The outside environment that the skin must endure may consist of large fluctuations in both temperature and humidity. Further, the skin may be exposed to radiation from the sun or other sources. Additionally, the skin is routinely exposed to wind, dust, dirt and other harsh chemicals. Finally, the skin must survive the daily rituals that may include washing, shaving, and/or the application of cosmetics.

These environmental factors contribute to what is often referred to as the premature aging of skin. In particular, these environmental factors have been known to cause aging lines, wrinkles, skin dryness characterized by the loss of the skin's natural oils and moisture, skin fading, age spots, and the loss of skin elasticity.

In addition, it is known that proper skin nutrition, characterized by the adequate supply and consistent replenishment of certain vitamins to the skin can both reduce the effects that environmental factors have on the skin, and may also reverse the signs of premature skin aging. Further, it is known that improper skin nutrition due to a deficiency of certain vitamins can cause premature aging, even in the absence of other environmental factors.

Recently, widespread use of tretinoin creams such as Retin-A® have been made in an attempt to reverse the premature aging of skin. Some evidence shows tretinoin may improve fine wrinkling, mottled hyperpigment-action and roughness associated with photodamage. Unfortunately, tretinoin creams are toxic, thus requiring supervision by a doctor and a prescription. Further, tretinoins often cause unwanted side effects such as local inflammation, redness, scaling, and a slight stinging sensation. Still further, tretinoin patients must limit sun exposure during use. Another treatment, that has seen recent use for the purpose of inhibiting premature aging are skin renewal acids such as alpha hydroxy acid. Although these renewal treatments may show some positive results in reversing the premature aging of skin, they are often accompanied by several unwanted side effects including dry skin and irritation. Further, renewal acid treatments are often criticized for producing results slowly.

In light of the above it is an object of the present invention to provide a safe and effective skin cream suitable for the purposes of softening the skin and preventing the premature aging of skin. It is another object of the present invention to provide a moisturizing skin cream that effectively delivers vitamins to the skin to ensure proper skin nutrition. It is yet another object of the present invention to provide a moisturizing skin cream suitable for application to the face and neck area. Yet another object of the present invention is to provide a moisturizing skin cream which is easy to use, relatively simple to manufacture, and comparatively cost effective.

None of the prior art methods have been found to be completely suitable to meet these needs and are cumbersome. The present invention provides such a method and the overall combination of these features is nowhere disclosed in the prior art cited above which appears to be representative of the general art in this area although it is not intended to be an all-inclusive listing of pertinent prior art patents.

SUMMARY

In light of the disadvantages of the prior art, the following summary is provided to facilitate an understanding of some of the innovative features unique to the present invention and is not intended to be a full description. A full appreciation of the various aspects of the invention can be gained by taking the entire specification, claims, and abstract as a whole.

The present invention is a facial moisturizer which is to be applied to the face and neck. The formula is a mixture of oils and essential oils which is to help moisturize and aid in common skin concerns.

Another embodiment of the invention is a mixture of oils and essential oils which is to help moisturize and aid in common skin problems.

In an alternative embodiment, the present invention effectively softens, moisturizes and provides a unique essential oils combination of needed nutrients to the skin.

It is principal object of the invention, by effectively softening, moisturizing, and supplying appropriate vitamins to the skin, the skin cream of the present invention effectively helps to prevent the premature aging of skin.

Another significant embodiment of the present invention provide an advantageously a single composition which moisturizes the skin and protect it at the same time. Thus, it is more convenient for a subject in need of such a composition and advantageously provide a great compliance. One embodiment of the present invention is a moisturizing composition comprising at least one moisturizer ingredient.

It is an object of the invention to provide a new skin moisturizer which may be easily and efficiently manufactured and marketed and which is of an effective and reliable construction.

The essential oils used herein according to present invention is selected from:
*Simmondsia Chinensis* Seed Oil (Jojoba)
*Rosa Moschata* Seed Oil (Rosehip)
*Daucus Carota* Stavia Seed Oil (Carrot)
Callophyllum Inophyllum Oil (Tamanu)
*Rosmarinus Officinalis* Leaf Oil (Rosemary)

*Boswellia Carterii* Oil (Frankincense)
*Pelargonium Graveolens* Oil (Geranium)
*Cymbopogon* Fleuosus Oil (Lemongrass)
*Helichrysum Italicum* Oil (Immortelle)

It is an object of the invention to provide a new skin moisturize which provides following benefits:
Moisturizer
Astringent (kills harmful germs and bacteria)
Balances hormones levels
Noncomedogenic (less likely to clog pores and cause breakouts)
Prevents acne and blackheads
Reduces dark circles, age spots, scars, fine lines and wrinkles
SPF protection
Anti-aging
Anti-fungal
Improves skin circulation
Rejuvenates skin.

This Summary is provided merely for purposes of summarizing some example embodiments, so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, and Claims.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

Unless otherwise defined, all terms (including technical and scientific terms) used herein have the same meaning as commonly understood by one having an ordinary skill in the art to which the invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques are disclosed. Each of these has individual benefit and each can also be used in conjunction with one or more, or in some cases all, of the other disclosed techniques. Accordingly, for the sake of clarity, this description will refrain from repeating possible combination in an unnecessary fashion. Nevertheless, the specifications and claim/s should be read with the understanding that such combinations are entirely within the scope of the invention and the claim/s.

The method of the present invention is that it relates to a facial moisturizer which is to be applied to the face and neck. The formula is a mixture of oils and essential oils which is to help moisturize and aid in common skin concerns. The particular formula consists of the following:
*Simmondsia Chinensis* Seed Oil (Jojoba)
*Rosa Moschata* Seed Oil (Rosehip)
*Daucus Carota* Stavia Seed Oil (Carrot)
Callophyllum Inophyllum Oil (Tamanu)
*Rosmarinus Officinalis* Leaf Oil (Rosemary)
*Boswellia Carterii* Oil (Frankincense)
*Pelargonium Graveolens* Oil (Geranium)
*Cymbopogon* Fleuosus Oil (Lemongrass)
*Helichrysum Italicum* Oil (Immortelle).

It is an object of the invention to provide a new skin moisturizer which provides following benefits:
Moisturizer
Astringent (kills harmful germs and bacteria)
Balances hormones levels
Noncomedogenic (less likely to clog pores and cause breakouts)
Prevents acne and blackheads
Reduces dark circles, age spots, scars, fine lines and wrinkles
SPF protection
Anti-aging
Anti-fungal
Improves skin circulation
Rejuvenates skin Another embodiment of the present invention relates to simple application where the moisturizing skin cream can be applied daily. To apply, a generous amount is first placed on the fingertips or an appropriate delivery device such as a sponge or cloth. Next, the cream is dabbed onto the skin at the area to be treated. Finally, the cream is rubbed into the skin using the fingertips until the cream becomes transparent. Use of the skin cream immediately after washing and towel drying the skin is recommended for maximum moisturizing effect.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A moisturizing formulation consisting essentially of
a *Simmondsia Chinensis* Seed Oil;
b. *Rosa Moschata* Seed Oil;

c. *Daucus Carota* Stavia Seed Oil;
d. Callophyllum Inophyllum Oil;
e. *Rosmarinus Officinalis* Leaf Oil,
f. *Boswellia Carterii* Oil;
g. *Pelargonium Graveolens* Oil;
h. *Cymbopogon* Fleuosus Oil; and
i. *Helichrysum Italicum* Oil;
wherein the moisturizing formulation is in the form of a cream.

* * * * *